(12) United States Patent
Ishihara et al.

(10) Patent No.: US 7,078,440 B2
(45) Date of Patent: Jul. 18, 2006

(54) DIMETHYL TEREPHTHALATE COMPOSITION AND PROCESS FOR PRODUCING THE SAME

(75) Inventors: Kenichi Ishihara, Matsuyama (JP); Kazumasa Mizuno, Matsuyama (JP); Minoru Nakashima, Matsuyama (JP); Kazuhiro Sato, Osaka (JP); Masanori Miyamoto, Matsuyama (JP); Taizo Mori, Matsuyama (JP)

(73) Assignee: Teijin Limited, Osaka (JP)

( * ) Notice: Subject to any disclaimer, the term of this patent is extended or adjusted under 35 U.S.C. 154(b) by 448 days.

(21) Appl. No.: 10/432,822

(22) PCT Filed: Nov. 22, 2001

(86) PCT No.: PCT/JP01/10241
§ 371 (c)(1),
(2), (4) Date: May 27, 2003

(87) PCT Pub. No.: WO02/42253
PCT Pub. Date: May 30, 2002

(65) Prior Publication Data
US 2004/0054019 A1 Mar. 18, 2004

(30) Foreign Application Priority Data

| Nov. 27, 2000 | (JP) | 2000-359137 |
| Nov. 29, 2000 | (JP) | 2000-362783 |
| Nov. 29, 2000 | (JP) | 2000-362784 |
| Nov. 29, 2000 | (JP) | 2000-362785 |
| Nov. 30, 2000 | (JP) | 2000-364633 |
| Dec. 1, 2000 | (JP) | 2000-366861 |
| Oct. 3, 2001 | (JP) | 2001-307289 |

(51) Int. Cl.
*C08J 11/22* (2006.01)
*C08J 11/24* (2006.01)

(52) U.S. Cl. .................... 521/48; 528/306.8; 528/496; 560/76; 560/78

(58) Field of Classification Search .................. 521/48, 521/48.5; 528/306.8, 496; 560/76, 78
See application file for complete search history.

(56) References Cited

U.S. PATENT DOCUMENTS 6,580,005 B1 * 6/2003 Yazaki et al. ............... 562/483
6,706,843 B1 * 3/2004 Ishihara et al. ............... 526/65

FOREIGN PATENT DOCUMENTS

| CN | 1067662 A | 8/1993 |
| CN | 1135476 A | 10/1997 |
| CN | 1188101 A | 7/1998 |
| JP | 43-2088 B | 1/1968 |
| JP | 43-2088 B1 | 1/1968 |
| JP | 57-95925 A | 6/1982 |
| JP | 11-300619 | * 11/1999 |
| JP | 11-302443 A | 11/1999 |
| JP | 2000-53802 A | 2/2000 |
| JP | 20000-53802 A | 2/2000 |
| JP | 2000-169623 A | 6/2000 |
| JP | 2000-239201 A | 9/2000 |

* cited by examiner

Primary Examiner—Peter Szekely
(74) Attorney, Agent, or Firm—Sughrue Mion, PLLC

(57) ABSTRACT

A dimethyl terephthalate composition includes 0.001 to 200 ppm of methyl 4-(1,3-dioxolan-2-yl)benzoate and 0 to 1 ppm of dimethyl hydroxyterephthalate contained in dimethyl terephthalate, and exhibits improved properties as a material for producing polyester.

8 Claims, No Drawings

DIMETHYL TEREPHTHALATE COMPOSITION AND PROCESS FOR PRODUCING THE SAME

TECHNICAL FIELD

The present invention relates to dimethyl terephthalate usable as a starting material for producing a polyester. More particularly, the present invention relates to a dimethyl terephthalate composition having improved properties and usable as a starting material for the production of a polyester, and a method for producing the same.

BACKGROUND ART

The dimethyl terephthalate (which will be referred to as DMT hereinafter) is a main starting material for production of polyethylene terephthalate (which will be referred to PET hereinafter), which is a polycondensate product of DMT with ethylene glycol (which will be referred to as EG hereinafter). The Witten-Hercules method can be cited as a typical method for producing DMT.

The method of the present invention for producing the DMT comprises oxidizing p-xylene (which will be referred to PX hereinafter) and methyl p-toluylate with air, esterifing the resulting oxidized reaction mixture with methanol (which will be referred to MeOH hereinafter) under high-temperature high-pressure conditions, and collecting and refining the DMT from the esterifying reaction mixture.

However, there are problems that DMT produced from PX (which will be referred to PX-DMT hereinafter) according to the above method causes a hydrolytic reaction to occur when the PX-DMT is brought into contact with steam or the like, and acid components are formed as by-products, and, thus, the acid value of the resultant PX-DMT increases; and that the reaction product mixture contains a large amount of dimethyl hydroxyterephthalate (which will be referred to as HDT hereinafter) produced as a by-product by the oxidizing reaction, and thus the product exhibits a high intensity of fluorescence due to the presence of HDT, and the color of the product is bad.

DISCLOSURE OF THE INVENTION

An object of the present invention is to solve the problems of the above prior arts and to provide a DMT composition having a controlled acid value, at a low level, and a good color.

BEST MODE FOR CARRYING OUT THE INVENTION

In the process of the present invention, firstly, methyl 4-(1,3-dioxolan-2-yl)benzoate (which will be referred to 4-DOMB hereinafter) must be prepared. The process of the production of 4-DOMB include (1) a method for obtaining the 4-DOMB by synthesis and (2) a method for utilizing a by-product from a process for recovering DMT from a polyalkylene terephthalate by using EG and MeOH. The object of the present invention can be achieved by using DMT including a small amount of the 4-DOMB, even derived from either one of the methods.

As the above synthetic method (1), 4-DOMB can be readily produced by subjecting equimolar amounts of 4-carbomethoxybenzaldehyde and EG to a thermal reaction procedure under ambient atmospheric pressure in the presence of a known general-purpose acidic catalyst and at a temperature of 80 to 150° C. In this method, it is important to remove water generated as a by-product by a dehydrating reaction. The removal of the by-product water can be effected by distilling off or by use of molecular sieves with high efficiency.

On the other hand, the method (2) for utilizing the by-product from the process for recovering the DMT is an extremely favorable method even in industrial aspects because the by-product can be directly utilized and the DMT composition containing the resulting 4-DOMB needs no subsequent refining operation.

In the above method (2), initially, the polyalkylene terephthalate is subjected to a depolymerizing reaction in the presence of a known depolymerization catalyst in EG. The polyalkylene terephthalate used herein includes polyethylene terephthalate, polytrimethylene terephthalate and polybutylene terephthalate. If necessary, the mixture obtained by the depolymerizing reaction is subjected to the procedures that an excessive amount of EG used in the depolymerizing reaction is withdrawn from the mixture, and the withdrawn EG is introduced, together with MeOH and a transesterifying reaction catalyst, into a reactor and subjected to a transesterifying reaction to produce crude DMT and an alkylene glycol. The resulting reaction mixture is subjected to cooling treatment and then to a centrifugal separation treatment to separate a cake of the crude DMT from the mixture solution.

A DMT composition containing the 4-DOMB in an amount within the range of 0.001 to 200 ppm can be obtained by, (A) carrying out operations to add MeOH, in a weight of 1 to 5 times based on the resulting cake, to the cake under conditions of 30 to 60° C. and then separate the resulting mixture again into the cake of the crude DMT and a mixture solution with the centrifugal separator, or (B) adjusting, for example the distillation column top temperature to 160 to 210° C. and the pressure to 2.7 to 13.3 kPa and performing control so that the reflux ratio is within the range of conditions of 0.1 to 2 when the resulting cake is distilled and purified. There is no problem at all if the methods (A) and (B) are used in combination.

As to the HDT, the HDT concentration must be minimized because the HDT concentration in the DMT directly contributes to increasing the fluorescence intensity of the DMT. However, there are problems that, generally, the PX-DMT is produced by an oxidation reaction of PX and thus the HDT is produced as a by-product, and the DMT produced as a final product contains 1 ppm or more of HDT.

However, when the method (2) utilizing the by-product of the process for recovering the DMT, is employed a DMT composition containing the HDT in a content of within the range of 0 to 1 ppm can be obtained.

As mentioned above, by utilizing a DMT composition containing the 4-DOMB within the range of 0.001 to 200 ppm and the HDT within the range of 0 to 1 ppm the increase in the acid value of the composition can be prevented, and a dimethyl terephthalate composition having a low fluorescence intensity, good color, and improved properties as the starting material for a polyester, can be obtained.

In the present invention, in the case of the above methods (A) and/or (B) in which the process for recovering the polyester is utilized, the 4-DOMB can be added, without problem, by either one of a batch method and a continuous method. Also, when the above-mentioned method (2) in which the by-product from the process for recovering the DMT is utilized and the process is carried out under the following conditions, the DMT composition containing the 4-DOMB and HDT within the scope of the present invention can relatively easily be obtained.

Namely, the depolymerizing reaction of the polyester with EG may usually be carried out at a temperature of 110 to 230° C. and a pressure (gauge pressure) of about 0.0 to 0.2 MPa. The depolymerizing reaction with EG is sufficiently carried out when the conditions are within the above-mentioned range. When the depolymerizing reaction temperature is below 110° C., the necessary depolymerizing time is extremely prolonged and the depolymerization is not efficient. On the other hand, when the depolymerizing reaction temperature exceeds 230° C., a reactor resistant to a high pressure must be employed and the depolymerization is unfavorable in consideration of the operational and the safety aspects.

When the transesterifying reaction with MeOH is conducted, the reaction temperature is preferably within the range of 50 to 150° C., and the reaction pressure (gauge pressure) is preferably within the range of 0.0 to 0.59 MPa. When the reaction temperature and reaction pressure are within the above-mentioned ranges, the transesterifying reaction can be sufficiently carried out. The transesterifying reaction time is preferably 30 minutes to 4 hours.

As either one of the depolymerizing reaction catalyst and the transesterifying reaction catalyst, conventional catalysts can be used; however, at least one type of metal salt compounds selected from the group consisting of carbonates, hydrogencarbonates and carboxylates of an alkali metal and an alkaline earth metal are preferably used, due to the high catalytic activity thereof. Furthermore, sodium carbonate is especially preferably used for both of the reaction catalysts.

In the mixture obtained by the transesterifying reaction, crude DMT, MeOH, EG and by-products produced during the depolymerizing reaction with EG and transesterifying reaction are present and the mixture further contains 4-DOMB, HDT, and others, for example, dioxane, dimethyl ether, water, etc.

In the case where the above-mentioned mixture is directly used to carry out recrystallizing operation, or crystals of DMT are not completely dissolved, the mixture is heated to perform a dissolving operation with a mixture solution. In this case, the mixture kept at the transesterifying reaction temperature is directly cooled to a temperature of 10 to 50° C. or, after the mixture is heated once to a temperature in the range of 60 to 150° C. in response to the composition of the mixture, it is then cooled to 10 to 50° C. If necessary, a latent heat of the solvent is preferably utilized to cool the mixture.

The DMT concentration in the mixture solution is preferably kept in the range of 10 to 40% by mass. When the DMT concentration is less than 10% by mass, the necessary amount of the solvent to be used may increase and an economical disadvantage may occur.

The recrystallization-treated mixture is subjected to a solid-liquid separation treatment using a centrifugal separator or the like, and then the resulting cake is washed with MeOH.

The amount of the MeOH mixed to the cake and the washing temperature are preferably in the range of 1 to 5 times the amount of the crude DMT cake and within the range of 30 to 60° C. to enhance the washing effects and handleability of the solid-liquid slurry and economical efficiency. The 4-DOMB contained in the crude DMT cake is incompletely removed by the washing step. The number of the washing operations applied to the cake is usually about one to three times but there is no problem when the number of the of washing operations is further increased.

After completing the washing with the MeOH and solid-liquid separation, the resultant crude DMT cake is heated and melted to thereby further remove the MeOH. The resultant DMT cake is finally distillation-refined under reduced pressure, and as a distilled fraction, a refined DMT is collected.

The distillation-refining procedure is performed under conditions of a reduced pressure of 2.7 to 13.3 kPa, a column top temperature of 160 to 210° C. and a reflux ratio of 0.1 to 2.0.

The vapor pressure of the 4-DOMB is somewhat lower than that of the DMT and a trace amount thereof may be contained in the resultant DMT composition as long as the vapor pressure is within the above-mentioned range. Excessively severe conditions in distillation-refining procedure are unfavorable because the detection of the 4-DOMB in the DMT composition becomes difficult. Also, an excessive intensification of the conditions should be avoided, because the distilling of the acid components causes an increase in acid value of the DMT composition.

Therefore, in order to cause the 4-DOMB to be contained in an adequate amount in the recovered DMT, it is particularly preferable from aspects of quality control that a distillation column having 5 to 20 plates expressed in terms of theoretical plates is used, and the operation conditions of the distillation are kept at a column top temperature of 180 to 195° C., in a reflux ratio of 0.3 to 1.0, and under a reduced pressure of 5.3 to 9.3 kPa.

On the other hand, as the amount of the HDT produced as a by-product in the depolymerizing reaction stage is very small, the concentration of HDT can be adjusted to a desired level by applying the above refining procedure.

In the present invention, the following system may be constructed to utilize the by-product produced in the above mentioned process for recovering the DMT.

Namely, when a recycling system, for the polyester, comprising producing materials for the production of polyester having a quality identical to that in trade by utilizing the process in which products available in trade and comprising as a principal component, a polyester, and wastes of products comprising a polyester as a principal component, and generated in the process for producing the polyester products are recovered from the trade; the recovered products and wastes are depolymerized with EG; and the depolymerization product is transesterified with MeOH to separate and refine the resultant crude DMT and EG; producing polyester products from the resultant materials for polyester; and supplying and circulating the polyester products in the trade, is constructed, it becomes possible to produce polyester products with a high degree of purity from polyester wastes which are now finally treated by incineration or landfilling disposal, and resources can effectively be utilized. The system will be illustrated in detail below.

A pretreating step for polyester wastes for example, polyester bottles, comprising, as a principal component, a polyester will be explained below. The wastes are pulverized preferably to a size of 2 to 30 mm square, more preferably 5 to 20 mm square, in the pretreating step from aspects of reactivity of the wastes in the reaction step or transportability of the wastes after the pretreating step. The reactivity of the wastes is improved by the pretreatment. When the wastes include the bottles having thickened portions which are formed to increase the mechanical strength and dimensional stability of the bottles by a crystallizing treatment or whitening treatment, the above-mentioned effects significantly appear at the thickened portions.

In the pulverizing step, the pulverizing capacity is preferably increased by using a two step-type pulverizing apparatus. That is, the wastes are roughly pulverized to a size of 30 to 150 mm square with a crusher for a first step and then pulverized to a size of 2 to 30 mm square with a crusher for the second step. When the wastes are directly pulverized to a size of 2 to 30 mm square with the crusher for the first step, a load applied to the crusher is too high and the pulverizing efficiency becomes low. When a magnetic separator for removing metal components is installed upstream to and/or downstream from the crusher for the first step, there are effects on a reduction in load on a cutter of the crusher for the second step. There are many cases where the pulverized material is contaminated with plastics different from the polyester such as polyethylene, polypropylene, polystyrene or polyvinyl chloride, contained as impurities in the wastes, which are used as material of caps, labels or the like for the polyester bottles.

In the system of the present invention, when the polyester wastes are contaminated with the above-mentioned different plastics, the reaction conditions can be established so that the purity of the recovered products is not decreased by a decomposition of the different plastics in the later reaction step. However, as the different plastics have a possibility of exerting unfavorable influences upon handling such as sticking to a reactor or causing clogging of filters, it is important that the different plastics are removed as much as possible in the pretreating step to suppress the contamination in the reaction step as far as possible to make the reaction proceed smoothly. Various steps for completely removing the different plastics as in the case of carrying out the material recycling, however, are not necessary, and only the necessity minimum steps are required.

It is preferable that the labels are initially removed from the pulverized wastes by air blow separation for removing a thin plastic film (polyethylene, polypropylene, polyvinyl chloride or the like) which is different from the polyester and used in the labels or the like. When the air flow rate is too high in this process, the polyester which is a useful component is removed in company with the labels, and thus, it is necessary to suitably adjust the air flow rate. Most of the labels comprising, as a principal component, polypropylene, polystyrene or polyvinyl chloride, can be removed by air blow separation.

The pulverized wastes is preferably treated with a decanter in order to remove the caps, which cannot be removed by the air blow separation, to remove the different plastics, for example, polypropylene and polyethylene, having a lower specific gravity than that of water by a centrifugal separation method. Since the decanter is used also as equipment for washing off impurities (soy sauce, soft drinks or the like) which are derived from foods or the like and remain in the wastes, with water, there is no problem at all if the contents remain in, for example, the bottles. The washing water separated by the centrifugal separation is recycled again to the decanter and a portion of the recycled washing water is delivered and subjected to wastewater treatment.

The pulverized wastes which are delivered from the decanter and washed with water (which wastes will be referred to recovered flakes hereinafter) are transported to a reactor, for the reaction step, by a pneumatic transportation means. When the size of the pulverized waste particles is adjusted to a relatively large size such as 30 to 150 mm square in the above-mentioned pulverizing step, problems such as deterioration of transportation efficiency or choking of rotary valves of the pneumatic transportation means occur. To solve the problems, preferably the wastes are pulverized to a size of about 2 to 30 mm square as in the present system. Moisture remains in the recovered flakes before the pneumatic transportation; however, from aspects of the reactivity of the wastes in the reaction step, the moisture content is preferably reduced to 0.2% or less based on the mass of the recovered flakes by drying the wastes during the pneumatic transportation or using a dryer or the like.

The pretreatment of the wastes comprising, as principal components, fibers, films or the like will be explained below. As the material, for example, nylon, polyethylene, polypropylene or cotton, which are different from the polyester cannot serve as an effective component, the wastes contaminated with a large amount of those material are preferably removed at a stage of acceptance. That is, the wastes are analyzed with a discriminating device such as a near-infrared ray spectrometer, and when the wastes exhibit an absorption pattern different from that of the polyester, the wastes are removed in this stage, without transporting the waste to the next step, to enhance the efficiency of the waste treatment.

It is preferable that the wastes passing through the inspection with the near-infrared ray analysis are granulated and solidified from aspects of handleability in the reaction step after the pretreating step or pneumatic transportation after the pretreating step. However, the direct charging of yarn wastes, film wastes or the like having a continuous structure into a granulater is extremely difficult, and thus, the wastes must be initially pulverized into an adequate size. The size of the pulverized waste particles is preferably 2 to 50 mm square. When the size of the pulverized waste particles is too large, in the next granulating step, unfavorable results, namely an insufficient solidification, occur. As a mode for carrying out the pulverization, preferably the pulverizing apparatus is of a two-stage type, to increase the pulverization efficiency. Namely, the polyester wastes are first crushed into a size of 30 to 150 mm square with a first crusher and then pulverized to a size of 2 to 50 mm square with a second crusher. When the wastes are directly pulverized to a size of 2 to 50 mm square with the first crusher, the load applied to the first crusher becomes to high, and the pulverization efficiency becomes low.

The pulverized wastes are subsequently charged into a granulater and formed into a cylindrical solid form. The width of the waste particles is preferably 2 to 20 mm, more preferably 4 to 6 mm. The length of the waste particles is preferably 2 to 60 mm. The granulating method is of the type of stuffing the pulverized polyester wastes into granulating holes of a specified size, partially melting the surface portions of the polyester waste particles by frictional heat generated on the polyester waste particle surfaces and solid-forming the pulverized wastes particle utilizing the melted portions as a binder. If size of the pulverized particles is too large, the amount of the generated frictional heat is the small and thus the pulverized particles surfaces are not sufficiently bonded to each other. When the bonding is insufficient as described above, the granulated waste particles are disintegrated by collision with pipes in the subsequent transportation step, and thus when the disintegrated particles are stored in a storage tank, the disintegrated waste particles form a bridging structure and thus are very difficult to discharge from the storage tank. The granulation procedure is performed at a temperature not lower than the glass transition point of the polyester and not higher than the melting point of the polyester.

Namely, in another granulating method, the wastes is heated to a temperature not lower than the melting point of the polyester, to completely melt the wastes, then the melt is granulated and cooled. However, in this granulating method, impurities such as nylon, in the wastes, are thermally decomposed due to high temperatures to deteriorate the quality of recovered products. Therefore it is preferable to perform the granulating method in which the polyester waste is heated at a temperature equal to or higher than the glass-transition point of the polyester and equal to or lower than 195° C., so as to pertially melt the surfaces of the waste particles and the bond the melted surfaces to each other. In this method, the handleability of the waste particles can be improved while suppressing the decomposition of the impurities and the decline of rate of reaction. It is needless to say that, in the above-mentioned method, there is no trouble at all even if the polyester wastes are contaminated with resin wastes.

The procedures for preparing a DMT composition and EG, which are principal materials for the polyester, from the polyester wastes will be explained below.

The polyester wastes which have been appropriately pulverized, washed and separated in the above-mentioned pulverization, washing and separating treatment in the procedures are subjected to a depolymerizing reaction procedure in the presence of a conventional depolymerization catalyst in EG. In this procedure, the depolymerizing conditions described above may be directly adopted for the depolymerizing reaction.

When the present recycling system is adopted, the depolymerizing reaction of the polyester with EG is preferably carried out at a temperature of 110 to 195° C. That is, if the depolymerizing reaction temperature is below 110° C., the depolymerizing time is extremely prolonged. On the other hand, if the depolymerizing reaction temperature is more than 195° C., in the case where the polyester wastes containing nylon are used as a raw material, the nylon is thermally decomposed and the resultant nitrogen compounds contaminate the DMT and EG and the quality of the resultant polyester products, produced by utilizing the DMT and EG, is unfavorably deteriorated.

The DMT composition obtained by the above-mentioned procedures is then used together with EG as a raw material for producing the polyester by using a conventional apparatus for producing a high-purity polymer. As EG to be used in this case, the EG obtained by the procedures in which the polyester wastes is subjected to a depolymerization reaction with EG; the resultant products are subjected to a transesterification reaction with MeOH; and the resultant crude DMT and EG are separated from each other and refined, is used.

A high-purity polyester polymer of the purity equal to or higher than that of the virgin polymer is obtained by the above-mentioned procedures, and various kinds of polyester products can be produced in the manner similar to that for the virgin materials by a conventional technique.

Although the method for producing the high-purity polymer is a well known method, for reference, the production method of a polyalkylene terephthalate resin composition will be explained below. A starting materials including the DMT composition and EG obtained by the above-mentioned production equipment are subjected to transesterification reaction procedure in the presence of a transesterification catalyst to prepare bis(β-hydroxyethyl)terephthalate and/or an oligomer thereof, then the transesterification product is subjected to a melt polycondensation procedure in the presence of a polycondensation catalyst and a stabilizer at a high temperature under a reduced pressure to provide a polyalkylene terephthalate resin composition.

The transesterification catalyst preferably comprises one or more members of salts of alkaline earth metals, for example, magnesium and calcium and compounds of metals, for example, titanium, zinc and manganese. The polycondensation catalyst preferably comprises one or more members of germanium compounds, antimony compounds, titanium compounds, cobalt compounds, tin compounds, etc.

The stabilizer preferably includes phosphate esters, for example, as trimethyl phosphate, triethyl phosphate and triphenyl phosphate; phosphite esters for example, triphenyl phosphite and trisdodecyl phosphite, acid phosphate esters, for example, methyl acid phosphate, dibutyl acid phosphate and monobutyl acid phosphate; and phosphorus compounds, for example phosphoric acid, phosphorous acid, hypophosphorous acid or polyphosphoric acid.

The transesterification catalyst may be fed during the preparation of the starting materials and further in the initial stage of the transesterification reaction. The stabilizer may be fed in or before the initial stage of polycondensation reaction; however, the stabilizer is preferably fed when the transesterification reaction is completed. Furthermore, the polycondensation catalyst may be fed in or before the initial stage of the polycondensation reaction. The reaction temperature during the transesterification is usually 200 to 260° C., and the reaction pressure is usually the ambient atmospheric pressure to 0.3 MPa. The reaction temperature in the polycondensation is usually 250 to 300° C., and the reaction pressure is usually 60 to 0.1 kPa. The transesterification and polycondensation reaction as mentioned above may be carried out in one stage or dividedly in plural stages. The polymer thus prepared has an intrinsic viscosity of usually 0.4 to 0.90 and is formed into chips by a conventional procedure. The average particle size of the polymer chips is within the range of usually 2.0 to 5.5 mm, preferably 2.2 to 4.0 mm. The polymer obtained by the melt polycondensation procedure as described above may be further subjected to solid-phase polymerization. The polymer chips fed to the solid-phase polymerization are preheated at a lower temperature than a temperature at which the solid-phase polymerization is carried out, to precrystallize and then the precrystallized polymer is fed to the solid-phase polymerization. In the precrystallization procedure, the polymer chips in an amorphous state are crystallized in one stage or two stages always under fluidized conditions so as not to cause the polymer chips to be melt-adhered to each other by heat generated by crystallization of the polymer chips. The next solid-phase polymerization procedure comprises at least one stage and is carried out at a polymerization temperature equal to or lower than the melt-adhering temperature of the polymer under conditions of a vacuum of 0.05 to 5 kPa or under a pressure of from the ambient atmospheric pressure to 0.1 MPa in a stream of an non-reactive gas, for example, nitrogen, argon or carbon dioxide. The solid-phase polymerization reaction time may become shorter with an increase in reaction temperature, but is usually 1 to 50 hours, preferably 5 to 30 hours, more preferably 10 to 25 hours.

The DMT composition of the present invention can be converted into terephthalic acid by a conventional procedure, for example, hydrolysis, and is used as a starting material for producing the polyester. Thereby, the already existing equipment can be utilized for producing the polyester polymer using the terephthalic acid as a starting material. The method for producing the high-purity polymer in this case is also a well-known. However, the method will be explained below for reference.

A starting material including the terephthalic acid and EG obtained by hydrolyzing the DMT composition of the present invention is subjected to a esterifying reaction procedure to prepare bis(β-hydroxyethyl)terephthalate and/or oligomers thereof, and the reaction product is subjected to a melt polycondensation procedure in the presence of a polycondensation catalyst and a stabilizer, at a high temperature under a reduced pressure, to provide the polymer. The use of the esterification catalyst is not especially necessary because terephthalic acid itself serves as an autocatalyst for the esterification reaction. Germanium compounds, antimony compounds, titanium compounds, cobalt compounds, tin compounds, etc. are generally known as polycondensation catalysts, however, the polycondensation catalyst to be used in the present invention is limited to germanium dioxide which can impart satisfactory color tone, transparency and hygienic property to the resultant polymer. The amount of the catalyst is preferably 20 to 150 ppm (based on the acid components of the polyester), more preferably 30–100 ppm, still more preferably 30 to 80 ppm, expressed in terms of the germanium element.

The stabilizer to be used for the polymerization preferably includes phosphate esters, for example, trimethyl phosphate, triethyl phosphate and triphenyl phosphate; phosphite esters, for example, triphenyl phosphite and trisdodecyl phosphite; acid phosphate esters, for example methyl acid phosphate, dibutyl acid phosphate and monobutyl acid phosphate; and phosphorus compounds, for example, phosphoric acid, phosphorous acid, hypophosphorous acid or polyphosphoric acid. The amount of the catalyst used is within the range of usually 5 to 1000 ppm, preferably 10 to 500 ppm, based on the total mass of polymerization materials and expressed in terms of the mass of the metal in the catalyst. The amount of the stabilizer used is within the range of usually 10 to 1000 ppm, preferably 20 to 500 ppm, based on the total mass of polymerization materials and expressed in terms of the weight of the phosphorus atom in the stabilizer.

The catalyst and stabilizer can be fed in an optional stage of the esterifying reaction and the transesterification in addition to the preparation of the starting material slurry, and can further be fed in the initial stage of the polycondensation reaction step. The reaction temperature in the esterification or transesterification procedure is usually 240 to 280° C., and the reaction pressure is from the ambient atmospheric pressure to 0.3 MPa. The reaction temperature in the polycondensation procedure is usually 250 to 300° C. The reaction pressure is usually 60 to 0.1 kPa. The esterification reaction or transesterification and polycondensation reaction may be carried out in one single step or dividedly in plural steps. The polymer thus obtained has an intrinsic viscosity of usually 0.45 to 0.70 and is formed into chips by a conventional procedure. The average particle size of the polymer chips is within the range of usually 2.0 to 5.5 mm, preferably 2.2 to 4.0 mm.

The polymer obtained as described above by the melt polycondensation procedure is usually further fed to the solid-phase polymerization. The polymer chips fed to the solid-phase polymerization are preheated at a lower temperature than the temperature at which the solid-phase polymerization is carried out, to precrystallize the polymer chips, and then they are fed to the solid-phase polymerization. In the precrystallization step, the polymer chips in an amorphous state are crystallized at a temperature of usually 120 to 200° C., preferably 130 to 180° C. in one stage or two stages for at least 15 minutes or more, while keeping the polymer chips in a fluidized condition to prevent the melt-adhesion of the polymer chips to each other due to the exothermic crystallization of the polymer chips.

The solid-phase polymerization comprises at least one stage and is carried out at a polymerization temperature of usually 190 to 230° C., preferably 195 to 225° C. under a vacuum of 0.05 to 5 kPa or under conditions of atmospheric pressure to 0.1 MPa under the flow of a non-reactive gas such as nitrogen, argon or carbon dioxide. The solid-phase polymerization time may become shorter with an increasing temperature, but is usually 1 to 50 hours, preferably 5 to 30 hours, more preferably 10 to 25 hours. The intrinsic viscosity of the polymer obtained by the solid-phase polymerization is within the range of usually 0.70 to 0.90.

In the present invention, the content of diethylene glycol (which will be referred to as DEG hereinafter) in the polyethylene terephthalate obtained by the above-mentioned procedure is 0.7 to 2.0% by mass, preferably 1.0 to 1.5% by mass, based on the total amount of the diol units constituting the polyethylene terephthalate. If the content of DEG is too low, the transparency of the bottle body section after molding is deteriorated. If the content of DEG is too high, the heat resistance of the product is decreased and, further, accelerating effects on crystallization are reduced. To adjust the content of DEG within the above range, the following methods may be employed. A method in which the DEG is used as a part of polymerization materials, and a method in which a portion of ethyleneglycol used as a principal material is converted to DEG, and thus the amount of DEG produced as a by-product is controlled while the reaction conditions are controlled.

Oligomer components which are contained in the polymer and are a main cause for metal mold staining during the molding of bottles, and acetaldehyde (which will be referred to AA hereinafter) components which are contained in the polymer and affect taste or smell of materials filled in the bottles, are preferably minimized. The oligomer content in the polymer is preferably 0.5% by mass or less, more preferably 0.4% by mass or less. The content of the AA in the polymer is preferably 5 ppm or less, more preferably 2 ppm or less.

Since the contents of the oligomers and AA are reduced by the above-mentioned solid-phase polymerization procedure, the target levels are achieved by controlling the intrinsic viscosity of the polymer after the melt polymerization, and the time and temperature of the solid-phase polymerization.

Furthermore, the concentration of terminal carboxyl groups of the polymer is especially preferably controlled in the range of from 15 to 25 eq/ton. When the concentration of the terminal carboxyl groups falls below the above-mentioned range, the solid-phase polymerizability of the resultant polymer is poor and a long time may be necessary to increase the intrinsic viscosity of the polymer to the target level. On the other hand, when the concentration is above the above-mentioned range, and when the polymer is subjected to the solid-phase polymerization, reduction effects on the content of cyclic trimeric oligomers may be poor.

The polyester polymer thus obtained can be formed into polyester films by a film-forming equipment to provide a group of various kinds of polyester film products, or converted into polyester yarns or fibers by a yarn manufacturing equipment to produce products such as clothes, carpets, interior automotive trims, futons (bedclothes) or flooring materials. The above-mentioned polymer can be used as a material for the production of PET bottles or engineering plastics by carrying out necessary treatment of the polymer with solid-phase polymerization equipment.

When the above-mentioned recycling system is utilized, the group of the original polyester products can be reproduced from the wastes containing the polyester. Thus, the nearly complete "circulation type recycling system" can be constructed.

Polyester products, not only the bottles made of the polyester but the fiber wastes, causing great problems at present, can readily be recycled to polyester products, and the necessity for environmental pollution type disposal such as landfilling or incineration as general industrial wastes is eliminated. Therefore, the recycling system is effective in enabling the solution to waste disposal problems and achievement of resource saving and energy saving.

The transesterifying equipment, crude DMT refining equipment, hydrolytic equipment, monomer producing equipment, polymer producing equipment, EG/MeOH refining equipment, etc. used in the system are already established as individual equipment. Thus, according to the present recycling system, when an improvement is applied to the pretreating equipment and depolymerization equipment, and the improved equipments are combined with the above-mentioned conventional equipments, a circulation type recycling system intended for polyester wastes such as used bottles, clothes, films, etc. made of polyester, can be constructed, to turn the polyester wastes into original products.

EXAMPLES

The contents of the present invention will be further explained, in specific detail, by the following examples which are not intended to limit the scope of the present invention in any way. Respective data in the examples are determined by the following methods:

(1) Qualitative Analysis of 4-DOMB and HDT:

A sample was subjected to recrystallizing and extracting procedures using acetone solvent and MeOH solvent, and the resulting extract was then concentrated. The concentrated sample was subjected to a qualitative analysis using gas chromatography (apparatus: HP5890 manufactured by Hewlett Packard Co.; capillary column: DB-17 manufactured by J&W Scientific, Inc.) in a guaranteed reagent acetone solvent.

(2) Quantitative Analysis of 4-DOMB and HDT:

A sample was subjected to recrystallization and extraction operations using acetone solvent and MeOH solvent, and the resulting extract was then concentrated. The concentrated sample was subjected to a quantitative analysis using GC-MASS (apparatus: GC/mass detector=HP6890/HP5973 manufactured by Hewlett Packard Co.; capillary column, DB-17 manufactured by J&W Scientific, Inc.) in a guaranteed reagent acetone solvent.

(3) Fluorescence Intensity of DMT:

A sample was subjected to a fluorescence intensity measurement at an excitation wavelength of 328 nm and a fluorescence wavelength of 454 nm in chloroform used as a measuring solvent. F-4500 manufactured by Hitachi, Ltd. was used as the fluorophotometer.

(4) Compositional Ratios of bis-β-hydroxyethylene terephthalate (which will be Referred to BHET hereinafter) and Lower Oligomer Components:

The compositional ratios were determined by using GPC (apparatus: L-4000 liquid chromatograph manufactured by Hitachi, Ltd., tetrahydrofuran solvent), by a conventional method.

(5) Alkali Transmittance of Terephthalic Acid:

A solution was obtained by using 7.5 g of terephthalic acid in 50 ml (2 mol/L) of an aqueous solution of potassium hydroxide, and the alkali transmittance was determined from transmittance at a wavelength of 340 nm with an optical path length of 1 cm according to the method described in "CHEMICAL ENGINEERING OF JAPA"N, vol. 58, No. 10, pp. 787–789 (published by THE SOCIETY OF CHEMICAL ENGINEERS, JAPAN, 1994).

(6) Intrinsic Viscosity:

A predetermined amount of a sample cut out from a chip or a molded product was weighted, dissolved in o-chlorophenol at a concentration of 0.012 g/ml and the resultant solution was subjected to a measurement of the intrinsic viscosity, at 25° C.

(7) Haze:

A measurement of haze of a sample cut out from a bottle body section to a size of 50 mm×50 mm was carried out with a color and color difference meter (MODEL1001DP) manufactured b Nippon Densyoku K.K. Content of AA:

(8) Content of AA

The content of AA was determined by freeze-pulverizing a sample, charging the pulverized sample into a vial, keeping the sample at 150° C. for 60 minutes and the content of AA in the sample was measured with a headspace-gas chromatograph manufactured by Hitachi, Ltd.

(9) Content of DEG:

A sample was decomposed with hydrazine, and measurement of DEG content of the decomposed sample was made by gas chromatography.

(10) Col-b:

A predetermined volume of a sample was taken, and measurement of $b^*$ value of the sample was made with a color machine CM-7500 model manufactured by Color Machine Co.

Reference Example 1

DMT manufactured in the form of a white briquette by Petrocel Temex S.A. was subjected to a microanalysis. As micro content components, p-toluic acid and monomethyl terephthalate as acid components; dimethyl isophthalate and dimethyl phthalate as isomers; and methyl group-substitution products, for example, methyl p-toluate, 4-carbomethoxybenzaldehyde and dimethyl (o-, m-, p-)phthalate as other esters were detected. However, 4-DOMB was not detected.

In the DMT briquette, 1.5 ppm of HDT was detected, and the fluorescence intensity of the DMT briquette was further measured, and the resultant intensity value was 900.

Reference Example 2

A high-purity terephthalic acid (which will be referred to as PTA hereinafter) manufactured by Mitsui Chemicals, Inc. was subjected to a measurement of alkali transmittance.

The measurement result was 91%.

Example 1

A 500-ml separable flask was charged with 200 parts of EG, and further charged with 1.5 parts of sodium carbonate and 50 parts of polyethylene terephthalate. The temperature of the resultant mixture was increased while stirring the mixture at a stirring speed of 100 rpm to provide an internal temperature of the flask of 185° C. The mixture was kept in the above-mentioned conditions for 4 hours to complete a depolymerizing reaction of the polymer. The resultant depolymerized product was then concentrated by a distillation procedure under a reduced pressure of 6.65 kPa to recover the resultant concentrate and 150 parts of EG as a distilled fraction.

The resultant concentrate was mixed with 0.5 part of sodium carbonate as a transesterification catalyst and 100 parts of MeOH, and the mixture was kept at a liquid temperature of 75° C., under the ambient atmospheric pressure at a stirring speed of 100 rpm for 1 hour to effect a transesterification reaction.

The obtained mixture was cooled to 40° C. and filtered through a 3G-4 filter made of glass. The crude DMT recovered on the filter was mixed into 100 parts of MeOH, heated to 40° C., while stirred to wash the crude DMT, and filtered again through a filter made of glass. The washing procedure was repeated twice.

The crude DMT collected on the filter was charged into a distillation apparatus and subjected to a distillation procedure under a reduced pressure of 6.65 kPa and a reflux ratio of 0.5. As a result, a DMT composition was obtained as a distilled fraction. The recovered distilled fraction was in an amount of 40 parts. The amount of DMT contained in the residue in the distillation column was 2 parts. The reaction yield of the DMT was 93% by mass based on the amount of the polyethylene terephthalate fed to the flask.

In the DMT composition refined by the distillation, 20 ppm of 4-DOMB and 0.5 ppm of HDT were detected. When the 4-DOMB and HDT in the recovered DMT are compared with standard 4-DOMB and HDT, respectively, by GC-MASS analysis, it was confirmed that the detected fragment ions were identical to each other and thus both of the compared compounds had the same structure as each other, respectively.

The resultant DMT composition had a degree of purity of 99.9% by mass or more, an acid value of 0.003 mg (KOH)/g (DMT) and a fluorescence intensity of 330. Other properties of the resultant DMT were equal to those of the standard DMT manufactured by Petrocel Temex S.A. in Reference Example 1.

Example 2

Steam is continuously blown into 40 parts of the DMT composition obtained in Example 1 while keeping the conditions of the DMT composition at a temperature of 250° C. under a pressure of 3.92 MPa, and excessive portion of the steam and produced MeOH were continuously withdrawn to promote a hydrolytic reaction of the DMT composition. The reaction almost quantitatively proceeded to produce 33 parts of terephthalic acid.

Into 30 parts of the resultant terephthalic acid, were mixed 60 parts of MeOH. After the terephthalic acid was washed with MeOH, while stirring at 40° C., the washed terephthalic acid was collected by filtration and dried. The alkali transmittance of the obtained terephthalic acid was measured. As a result, the alkali transmittance was 90%, and no meaningful difference in the alkali transmittance between the resultant terephthalic acid and the PTA manufactured by Mitsui Chemicals, Inc. was found.

Example 3

A separable flask was charged with 40 parts of the DMT composition obtained in Example 1 and 75 parts of EG, and the resultant mixture was heated with stirring at 100 rpm. When the temperature reached about 200° C., MeOH was generated. The initiation of reaction was confirmed. The distilled MeOH fraction was delivered to the outside of the system through two separation columns, and EG and DMT fractions distilled together with MeOH were separated from MeOH and returned into the flask.

The above mentioned operations were repeated, and the reaction was terminated when the inside temperature of the flask reached a temperature of 220 to 250° C. The necessary reaction time was about 8 hours.

The composition of the resultant mixture was analyzed by gas chromatography, and it was found that the DMT completely disappeared in the reaction. The BHET existing in an amount of 45% by mass was confirmed by the above-mentioned GC analysis and a GPC analysis. Other components respectively exhibited a sharp molecular weight distribution, and it could be confirmed that the other components were lower oligomers of dimers to pentamers.

Example 4

The DMT composition obtained in Example 1 was used as a starting material to produce PET according to a conventional method. Manganese acetate catalyst was used, and a transesterification (EI) reaction was carried out under the ambient atmospheric pressure until the reaction temperature reached 245° C. to produce lower oligomers comprising, as a principal component, BHET. Antimony trioxide was subsequently added to the resulting lower oligomers comprising, as a principal component BHET, and the mixture was subjected to polymerization at 290° C. under a high vacuum of 0.1 kPa for 1.8 hours. The intrinsic viscosity of the resultant polymer was 0.70. The analytical results in another characteristics such as color, thermal characteristics and the content of DEG were almost the same as those of a polymer produced from the DMT manufactured by Petrocel Temex S.A. shown in Reference Example 1.

A gas chromatographic analyser equipped with a headspace sampler device (HS40XL manufactured by Perkin Elmer Corp.) was used to detect volatile components of the obtained polymer under conditions of 200° C. for 60 minutes. As a result, no 4-DOMB or HDT was detected.

Comparative Example 1

The same procedures as in Example 1 were carried out except that the vacuum distillation of crude DMT was carried out under distillation conditions of a reduced pressure of 6.65 kPa and a reflux ratio of 0.05, to provide a DMT composition as a distilled fraction. The disitilled fraction was recovered in an amount of 40 parts, amount of the residue in the bottom of the distillater were measured, and the amount of the DMT was determined. As a result, the amount of DMT was 2 parts. The reaction yield of the DMT based on the amount of the charged polyester was 93% by mass.

In the DMT composition refined by the distillation, 40 ppm of 4-DOMB and 1.1 ppm of HDT were detected.

With respect to the quality of the refined DMT composition, the DMT composition had a degree at purity of 99.9% by mass or more and an acid value of 0.003 mg (KOH)/g (DMT), and a exhibited a high fluorescence intensity of 700.

Comparative Example 2

The same procedures as in Example 1 were carried out except that the resulting mixture obtained by the transesterification reaction was cooled to 40° C. and filtered through a 3G-4 filter made of glass. The crude DMT collected on the filter was mixed in an amount of 45 parts into 40 parts of MeOH. The resultant mixture was heated to 40° C., stirred to wash the crude DMT with MeOH and refiltered through a filter made of glass. The washing was repeated twice.

A distillation apparatus was charged with the crude DMT which was collected on the filter, the charged DMT was distilled under a reduced pressure of 6.65 kPa and a reflux ratio of 0.5, to collect DMT as a distilled fraction. The distilled fraction was recovered in an amount of 40 parts. The amount of the residue in the bottom of the distillation apparatus was measured, and the amount of the DMT in the residue was determined. The amount of DMT was 2 parts. The reaction yield of the DMT based on the amount of the charged polyester was 93% by mass.

In the DMT composition refined by the distillation, 250 ppm of 4-DOMB and 0.5 ppm of HDT were detected.

With respect to the quality of the refined DMT composition, the degree of purity was 99.8% by mass, and the acid value was 0.01 mg (KOH)/g (DMT). A DMT composition which had the quality equal to that of the DMT manufactured by Petrocel Temex S.A., shown in Reference Example 1, could not be obtained.

Example 5

Bales (120 kg bales having bale dimensions: 900 mm×1000 mm×550 mm) of polyester bottles which were classified, collected and recovered by municipalities were opened, and then the polyester bottles was fed into a front crusher, having a screen opening diameter of the crusher established at 75 mm and pulverized by the front crusher. The resulting crushed material was then charged into a second crusher in which the screen opening diameter of the crusher was established at 10 mm, and pulverized in the second crusher.

The resultant pulverized material was subsequently treated with an air blow separator to remove labels, attached to the polyester bottles, and comprising, as principal components, polyethylene, polystyrene and/or polypropylene. Then, centrifugal separation with a decanter was applied to the separated fraction to remove caps of the bottles comprising as a principal component, polypropylene or polyethylene and labels which were not removed by the air blow separation, while washing off the contents of the bottles with water and removing the contents. Thereby, recovered flakes were obtained. The resultant recovered flakes in an amount of 100 kg were transported to a reaction step by pneumatic transportation.

In the reaction step, the recovered flakes were charged into a mixture consisting of 400 kg of EG with 3 kg of sodium carbonate and preheated to 185° C. and the mixture was subjected to a reaction under the ambient atmospheric pressure for 4 hours. Plastics other than the polyester, for example, polystyrene, which could not be removed in the pretreating step and floated to the EG liquid surface, were removed herein by solid-liquid separation. After completing the reaction, EG was distilled off in an amount of 300 kg under conditions of 140 to 150° C. and a pressure of 13.3 kPa. After distilling off the EG, the resultant residue in an amount of 200 kg was mixed with 3 kg of sodium carbonate and 200 kg of MeOH. The mixture was subjected to a reaction at 75 to 80° C. under the ambient atmospheric pressure for 1 hour.

After completing the reaction, the reaction liquid was cooled to 40° C., subjected to solid-liquid separation using a centrifugal separation, and separated into a cake comprising, as a principal component, a crude DMT and a filtrate comprising as principal components, MeOH and crude EG. The crude DMT recovered by the solid-liquid separation was mixed into 200 kg of MeOH, the mixture was heated to 40° C. and stirred, to wash the crude DMT, and the mixture was further subjected to a solid-liquid separation by centrifugal separation. The washing procedure was repeated twice.

The resulting crude DMT was then refined by distillation under conditions of a pressure of 6.7 kPa and a reflux ratio of 0.5, and the crude EG was refined by distillation under conditions of a pressure of 13.3 kPa and a column bottom temperature of 140 to 150° C. As results, a DMT composition and EG were finally obtained in a yield of about 85%, respectively. The recovered DMT composition was by no means inferior to commercially available products in inspection items of appearance, acid value, melting colorimetry and sulfuric acid ash content. In the DMT composition, 22 ppm of 4-DOMB and 0.6 ppm of HDT were detected.

The resultant DMT composition was hydrolysed, and the resultant terephthalic acid (which will be referred to as recycled TA hereinafter) in an amount of 40 kg was mixed with 22 kg of ethylene glycol to provide a slurry. The slurry was fed into a polycondensation vessel and subjected to an esterifying reaction at 275° C. under the ambient atmospheric pressure for 4 hours. The reaction was carried out until the esterifying conversion rate reached 97%, while water generated as a by-product was discharged to the outside of the system, to prepare oligomers having a degree of polymerization of 5 to 10. To the prepared oligomers, 0.017 kg of an EG solution of phosphoric acid (at a concentration of 5.5% by weight in terms of phosphorus element) and 0.38 kg of an ethylene glycol solution of germanium dioxide (at a concentration of 1% by weight expressed in terms of germanium dioxide) were mixed. The mixture was subjected to a polycondensation under a reduced pressure of 2 kPa for 1 hour and then at 277° C. under a reduced pressure of 133 Pa for 2 hours. The produced polymer was withdrawn in the form of a strand, from a takeout port which was provided at the bottom of the polycondensation vessel and directly connected to a cooling water tank, the withdrawn product was cooled with water and then cut into the form of chips to prepare polymer chips.

The resulting polymer chips were subsequently crystallized in a stir-fluidizing type crystallizer, then dried at 140° C. under the flow of a nitrogen gas for 3 hours, subsequently transferred to a packed column type solid-phase polymerization column and subjected to the solid-phase polymerization at 215° C. under the flow of nitrogen for 22 hours, to produce a polyethylene terephthalate resin composition in the form of chips.

The resultant polyethylene terephthalate resin composition chips had an intrinsic viscosity of 0.75, a content of DEG of 1.3% by mass, a content of AA of 1.5 ppm and a Col-b$^{(*)}$ value of −1.0.

The chips were dried at 160° C. for 5 hours by using a dryer and then injection-molded by using an injection molding machine ("M-100DM" manufactured by Meiki Co., Ltd.) at a cylinder temperature of 275° C., a number of revolutions of screw of 160 rpm, a primary pressing time of 3.0 seconds, a mold temperature of 10° C. and a cycle time of 30 seconds to produce a cylindrical preform having an outside diameter of about 28 mm, an inside diameter of about 19 mm, a length of 136 mm and a mass of about 56 g. The resulting preform had an intrinsic viscosity of 0.69 and a content of AA of 12 ppm, and the moldability and appearance of the preform were good.

The surface of the preform was subsequently preheated to a temperature of about 110° C. by using an infrared ray heater, subjected to stretch blow molding procedure using a blow molding machine under a blowing pressure of 5 to 40 kg/cm$^2$ at a metal mold temperature of 150° C., to produce bottles having an average wall thickness in the body section of 330 μm and an internal volume of about 1.5 liters. The resultant bottles had a haze of 0.8% and exhibited good moldability and appearance.

Example 6

An absorption spectrum of 100 kg of a mixed waste of polyester fiber wastes which were generated from a polyester production process and contained no dye, with polyester film wastes, was measured by a near-infrared ray analyzer and it was found the measured absorption pattern was identical to that of polyester.

The whole amount of the mixed waste was then charged into a front crusher, and primarily crushed. In this front crusher the screen opening size of the front crusher was set at 75 mm. The resultant crushed waste was then charged into a second crusher, and secondarily crushed. In this second crusher, the screen opening size of the crusher was set at 20 mm. The resultant crushed waste was subsequently charged into a granulater operated at an internal temperature of 170° C., to produce granules having a diameter of 4 mm and a length of 45 mm, and then the resultant granules were transported to a reaction step through a pneumatic transportation means. The bulk density of the granulated wastes transported to the reaction step was 0.40 g/cm$^3$.

In the reaction step, 100 kg of the resulting granulated waste was mixed into a mixture of 400 kg of EG and 3 kg of sodium carbonate which were preheated to 185° C. The mixture was subjected to a reaction under the ambient atmospheric pressure at the above-mentioned temperature, for 4 hours.

After completing the reaction, 300 kg of EG was distilled off from the reaction product under conditions of 140 to 150° C. and a pressure of 13.3 kPa, and 3 kg of sodium carbonate and 200 kg of MeOH were added to 200 kg of the residue after the EG was distilled off the EG, and the mixture was subjected to a reaction at 75 to 80° C. for 1 hour.

After the reaction was completed, the resultant reaction liquid was cooled to 40° C., subjected to solid-liquid separation by which the reaction liquid was separated into a cake comprising, as principal component, crude DMT, and a filtrate comprising, as principal components, MeOH and a crude EG, by centrifugal separation. The crude DMT recovered by the solid-liquid separation was mixed into 200 kg of MeOH, the mixture was heated at 40° C. and stirred, to wash the crude DMT and then subjected again to solid-liquid separation by centrifugal separation. The washing operation was repeated twice.

The crude DMT was refined by distillation under conditions of a pressure of 6.7 kPa and a reflux ratio of 0.5 and the crude EG was refined by distillation under conditions of a pressure of 13.3 kPa and a column bottom temperature of 140 to 150° C. As a result, a DMT composition and EG were finally obtained in a yield of 85%, respectively. The recovered DMT composition was by no means inferior to commercially available DMT composition in inspection items of appearance, acid value, melt colorimetry and sulfuric acid ash content, and in the DMT composition, 25 ppm of 4-DOMB and 0.6 ppm of HDT were detected.

The recovered EG was by no means inferior to commercially available EG in inspection items of content of DEG, moisture content and melt colorimetry.

Then, 50 kg of the resulting DMT composition and 32 kg of EG were subjected to a transesterification reaction using a transesterification catalyst comprising tetra-t-butoxytitanium while MeOH generated as a by-product was distilled away to the outside of the reaction system. Then, the reaction mixture was further mixed with germanium dioxide as a polymerization catalyst and the resultant mixture was subjected to a transesterification reaction, while the mixture was heated to a temperature to 250° C. At a stage in which the distilling off of the MeOH was almost completed, orthophosphoric acid as a stabilizer was added to complete the transesterification reaction.

The reaction product was subjected to polycondensation reaction at a high temperature under a high vacuum. A polymer having an intrinsic viscosity of 0.60 was obtained. The resultant polymer was subsequently subjected to solid-phase polymerization procedure to produce a polyalkylene terephthalate resin composition having an intrinsic viscosity of 0.83, a Col-b* value of 2, a content of DEG of 1.8% by mass and a content of AA of 2 ppm.

The resultant polyalkylene terephthalate resin composition was dried at 160° C. for 5 hours by using a dryer and then, in a first working example, the dried resin composition was subjected to an injection molding procedure using an injection molding machine ("M-100DM" manufactured by Meiki Co., Ltd.) at a cylinder temperature of 275° C., a number of revolutions of screw of 160 rpm, a primary pressing time of 3.0 seconds, a metal mold temperature of 10° C. and a cycle time of 30 seconds to form cylindrical preforms having an outside diameter of about 28 mm, an inside diameter of about 19 mm, a length of 136 mm and a mass of about 56 g.

The intrinsic viscosity of the resultant preforms was 0.77 and the appearance and injection moldability were good. The surfaces of the preforms were subsequently preheated to a temperature of about 110° C. with an infrared ray heater, and the preheated preforms were subjected to a blow draw-molding procedure using a blow molding machine under a blowing pressure of 5 to 40 kg/cm$^2$ and a mold temperature of 150° C. and molded into bottles having an average wall thickness in the body section of about 330 μm and an internal volume of about 1.5 liters. The haze of the bottles was 0.9%, and the drawability was good.

In a second working example, a sheet having a film thickness of 0.5 mm was produced from the dried polyalkylene terephthalate resin composition by using a vented bi-axial extruder, subsequently heated at a sheet surface temperature of 100° C. and thermoformed into a tray with compressed air. The haze of the resultant tray was 1.0%, and moldability thereof was good.

Reference Example 3

The same procedures as in Example 5 were carried out except that the terephthalic acid was replaced by PTA manufactured by Mitsui Chemicals, Inc. The resultant polyethylene terephthalate resin composition had an intrinsic viscosity of 0.75, a Col-b* value of −1.5, a content of DEG of 1.3% by mass and a content of AA of 1.3 ppm.

The resin composition was subjected to the same injection molding procedure as in Example 5, to produce performs, and the resultant preforms had an intrinsic viscosity of 0.69 and a content of AA of 12 ppm, and moldability and appearance were good. Also, the resin composition was subjected to the same blow molding procedure as in Example 1, to provide bottles. The resultant bottles had a haze of 1.0% and moldability and appearance of the bottles were good.

Reference Example 4

The same procedures as in Example 6 were carried out, except that DMT manufactured by Teijin Ltd. was used in place of the DMT used in Example 6. A polyalkylene terephthalate resin composition having an intrinsic viscosity of 0.82, a Col-b of 2, a content of DEG of 1.8% by weight and a content of AA of 2 ppm was obtained.

The resultant polyalkylene terephthalate resin composition was molded into preforms in the same manner as in Example 6. The resultant preforms had an intrinsic viscosity of 0.76, and appearance and injection moldability of the preforms were good. Also, the resin composition was subjected to a blow molding procedure in the same manner as in Example 6, to form bottles. The resultant bottles had a haze of 0.9%, and the drawability of the bottles was good.

Furthermore, a tray obtained from the resin composition by thermoforming in the same manner as in Example 6 had a haze of 1.1%, and moldability thereof was good.

Comparative Example 3

The same procedures as in Example 5 were carried out, except that polyester wastes prepared by cutting a polyester and nylon blended yarn uniform wastes into a size of 10 to 20 mm square were used as fiber wastes; the fiber wastes in an amount of 100 kg was mixed with 65 kg of EG; and the mixture was subjected to a depolymerization reaction procedure under conditions of 205° C. and an internal pressure of 0.25 MPa.

The quality of the resulting DMT composition was significantly worse than that of commercially available products in all the inspection items of appearance, acid value, melt colorimetry and sulfuric acid ash content. The recovered DMT and EG were contaminated with nitrogen compounds and could not be reused as materials for polyester products. In the resultant DMT composition, 30 ppm of 4-DOMB and 1.1 ppm of HDT were detected.

INDUSTRIAL APPLICABILITY

A dimethyl terephthalate composition, improved in characteristics as a starting material for a polyester, can be provided according to the present invention.

When a by-product from a process for recovering DMT is utilized as the dimethyl terephthalate composition of the present invention, a recycling system for polyester wastes can be constructed. This system is a circulation type recycling system capable of producing dimethyl terephthalate and ethylene glycol each having a high degree of purity from usual polyester wastes containing the polyester (for example PET bottles, uniforms, futons (bedclothes), films, etc.), reproducing a group of polyester products using the dimethyl terephthalate and ethylene glycol as starting materials and recycling the used polyester products into polyester products having a quality equal to that of the original products. Thereby, the necessity for performing landfilling or incinerating treatment of general industrial wastes is eliminated, and resource saving or energy saving can be achieved.

The invention claimed is:

1. A dimethyl terephthalate composition comprising, as a principal composition, dimethyl terephthalate, and further containing 0.001 to 200 ppm of methyl 4-(1,3-dioxolan-2-yl)benzoate and 0 to 1 ppm of dimethyl hydroxyterephthalate.

2. A method for producing a dimethyl terephthalate composition comprising, as a principal component, dimethyl terephthalate, and further containing 0.001 to 200 ppm of methyl 4-(1,3-dioxolan-2-yl)benzoate and 0 to 1 ppm of dimethyl hydroxyterephthalate, comprising: subjecting a polyalkylene terephthalate to a depolymerization reaction with ethylene glycol; subsequently subjecting the resulting mixture to a transesterification reaction with methanol, to produce crude dimethyl terephthalate and an alkylene glycol; applying a cooling treatment to the reaction mixture; carrying out operations to separate the reaction mixture into a cake of crude dimethyl terephthalate and a mixture solution by using a centrifugal separator; and then distillation-refining the cake to provide a dimethyl terephthalate composition, characterized in that the reflux ratio during the distillation-refining step is controlled to 0.1 to 2.

3. The method for producing the dimethyl terephthalate composition according to claim 2, wherein the polyalkylene terephthalate comprises at least one member selected from the group consisting of polyethylene terephthalate, polytrimethylene terephthalate and polybutylene terephthahate.

4. A method for producing a dimethyl terephthalate composition comprising, as a principal component, dimethyl terephthalate and further containing 0.001 to 200 ppm of methyl 4-(1,3-dioxolan-2-yl)benzoate and 0 to 1 ppm of dimethyl hydroxyterephthalate, comprising: subjecting a polyalkylene terephthalate to a depolymerization reaction with ethylene glycol; subsequently subjecting the resulting mixture to a transesterification reaction with methanol, to produce crude dimethyl terephthalate and an alkylene glycol; applying a cooling treatment to the reaction mixture; separating the reaction mixture into a cake of crude dimethyl terephthalate and a mixture solution by using a centrifugal separator; and then distillation-refining the cake to provide a dimethyl terephthalate composition, characterized in that methanol is added in an amount of 1 to 5 times the mass of the cake obtained by centrifugal separating operation to the cake under conditions of 30 to 60° C.; then the resulting mixture is again subjected to a separation operations to separate a cake of dimethyl terephthalate from a mixture solution by using a centrifugal separator; and then the resultant cake is subjected to a distillation refining procedure.

5. The method for producing the dimethyl terephthalate composition according to claim 4, wherein the polyalkylene terephthalate comprises at least one selected from the group consisting of polyethylene terephthalate, polytrimethylene terephthalate and polybutylene terephthalate.

6. A method for producing terephthalic acid, employing as a starting material, a dimethyl terephthalate composition consisting, as a principal component, dimethyl terephthalate and further containing 0.001 to 200 ppm of methyl 4-(1,3-dioxolan-2-yl)benzoate and 0 to 1 ppm of dimethyl hydroxyterephthalate.

7. A method for producing bis(β-hydroxyethyl)terephthalate, employing as a starting material, a dimethyl terephthalate composition comprising, as a principal component, dimethyl terephthalate and further containing 0.001 to 200 ppm of methyl 4-(1,3-dioxolan-2-yl)benzoate and 0 to 1 ppm of dimethyl hydroxyterephthalate.

8. A method for producing a polyalkylene terephthalate, employing, as a starting material, a dimethyl terephthalate composition consisting, as a principal component, dimethyl terephthalate and further containing 0.001 to 200 ppm of methyl 4-(1,3-dioxolan-2-yl)benzoate and 0 to 1 ppm of dimethyl hydroxyterephthalate.

* * * * *